(12) United States Patent
Tu et al.

(10) Patent No.: US 10,215,798 B2
(45) Date of Patent: Feb. 26, 2019

(54) HIGH-TEMPERATURE TEST FIXTURE

(71) Applicants: R&D CENTER, SHANGHAI INSTITUTE OF CERAMICS, Shanghai (CN); SHANGHAI INSTITUTE OF CERAMICS, CHINESE ACADEMY OF SCIENCES, Shanghai (CN)

(72) Inventors: Xiaoniu Tu, Shanghai (CN); Yanqing Zheng, Shanghai (CN); Haikuan Kong, Shanghai (CN); Erwei Shi, Shanghai (CN)

(73) Assignees: R&D CENTER, SHANGHAI INSTITUTE OF CERAMICS, Shanghai (CN); SHANGHAI INSTITUTE OF CERAMICS, CHINESE ACADEMY OF SCIENCES, Shanghai (CN)

( * ) Notice: Subject to any disclaimer, the term of this patent is extended or adjusted under 35 U.S.C. 154(b) by 185 days.

(21) Appl. No.: 15/327,501

(22) PCT Filed: Jul. 25, 2014

(86) PCT No.: PCT/CN2014/083039
§ 371 (c)(1),
(2) Date: Jan. 19, 2017

(87) PCT Pub. No.: WO2016/011664
PCT Pub. Date: Jan. 28, 2016

(65) Prior Publication Data
US 2017/0160336 A1    Jun. 8, 2017

(30) Foreign Application Priority Data
Jul. 23, 2014 (CN) .......................... 2014 1 0352594

(51) Int. Cl.
*G01K 13/00* (2006.01)
*G01K 17/00* (2006.01)
(Continued)

(52) U.S. Cl.
CPC ......... *G01R 31/281* (2013.01); *G01N 27/041* (2013.01); *G01R 1/0458* (2013.01);
(Continued)

(58) Field of Classification Search
CPC ...... G01K 17/00; G01K 13/00; G01K 15/007; G01K 7/02
(Continued)

(56) References Cited

U.S. PATENT DOCUMENTS 4,393,718 A * 7/1983 Gebhard .................. G01N 3/04
374/49
4,399,545 A * 8/1983 Harmsen .................. F27B 3/085
373/105
(Continued)

FOREIGN PATENT DOCUMENTS

CN    201732101 U    2/2011
CN    203241441 U    10/2013
(Continued)

OTHER PUBLICATIONS

ISA State Intellectual Property Office of the People's Republic of China, International Search Report Issued in Application No. PCT/CN2014/083039, dated Jan. 15, 2015, WIPO, 5 pages.

*Primary Examiner* — Gail Kaplan Verbitsky
(74) *Attorney, Agent, or Firm* — Alleman Hall Creasman & Tuttle LLP

(57) ABSTRACT

A high temperature fixture, said fixture comprising: at least three noble metal electrodes arranged in parallel, among which two adjacent noble metal electrodes are used for clamping a test sample; noble metal wires connected to the
(Continued)

noble metal electrodes at one end, and to a test device at the other end for transmitting test signals generated by the test sample to the test device through the noble metal electrodes; and a thermocouple for measuring the temperature of the test materials.

12 Claims, 1 Drawing Sheet

(51) Int. Cl.
    *G01K 7/02*     (2006.01)
    *G01R 31/28*     (2006.01)
    *G01R 27/02*     (2006.01)
    *G01R 1/04*     (2006.01)
    *G01R 19/22*     (2006.01)
    *G01N 27/04*     (2006.01)

(52) U.S. Cl.
    CPC ......... *G01R 1/0491* (2013.01); *G01R 19/225* (2013.01); *G01R 27/02* (2013.01); *G01R 2019/24* (2013.01)

(58) Field of Classification Search
USPC .... 324/451, 750.01, 750.16, 750.19, 750.24, 324/750.03
See application file for complete search history.

(56) References Cited

U.S. PATENT DOCUMENTS

| | | | | |
|---|---|---|---|---|
| 4,529,869 | A * | 7/1985 | Ekstrom, Jr. | H05B 6/14 219/530 |
| 4,742,715 | A * | 5/1988 | Heinz | C21C 5/4673 374/E1.02 |
| 5,620,255 | A * | 4/1997 | Cook, III | A47J 43/28 374/141 |
| 6,179,846 | B1 * | 1/2001 | McFadden | A61B 90/14 602/37 |
| 9,222,844 | B2 * | 12/2015 | Rud | G01K 7/20 |
| 2006/0191907 | A1 * | 8/2006 | Henley | B23K 37/006 219/617 |
| 2007/0116087 | A1 * | 5/2007 | Hsu | G01K 1/143 374/147 |
| 2007/0242260 | A1 * | 10/2007 | Thorne | B01L 3/505 356/36 |
| 2009/0268780 | A1 * | 10/2009 | Liu | G01K 1/146 374/179 |
| 2010/0117390 | A1 * | 5/2010 | Tygard | B66C 1/427 294/81.51 |
| 2013/0208758 | A1 * | 8/2013 | Towner | A62C 37/50 374/1 |
| 2015/0289876 | A1 * | 10/2015 | Lazic | A61B 17/1227 606/153 |

FOREIGN PATENT DOCUMENTS

| | | | | |
|---|---|---|---|---|
| EP | | 41755 A | * | 8/1980 |
| JP | | 406137955 A | * | 6/1994 |

* cited by examiner

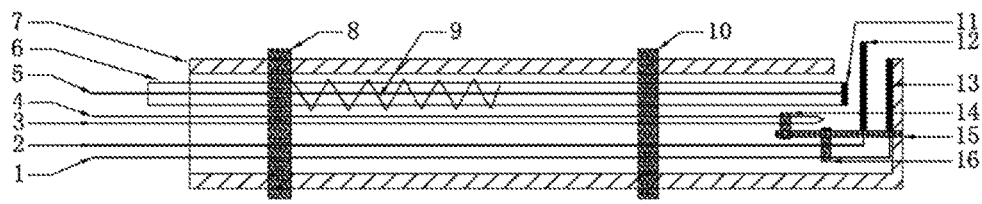

HIGH-TEMPERATURE TEST FIXTURE

FIELD OF THE INVENTION

The present invention belongs to the field of material property testing, and in particular relates to a fixture suitable for testing the electrical properties of a material at a high temperature.

BACKGROUND OF THE INVENTION

Sensors made of high-temperature resistant piezoelectric materials are widely used to test a series of in situ working data of the tested system under high temperatures (400° C.~1600° C.). Being first-hand data obtained in situ, these data provide a more comprehensive, reliable and accurate grasp on the working status of the whole system. For example, high-temperature pressure sensors made with lanthanum gallium silicate crystal (langasite) can be used to monitor the internal pressure of the engine cylinders in engines for spacecraft, aircraft, and automobiles, etc. The engine cylinder pressure monitored in real time can provide important engine operating parameters. These parameters can not only be used to analyze whether the engine is under normal operation, but also detect the engine cylinder combustion. By analyzing the data collected by the sensor, the life of the engine can be extended and the combustion efficiency of the fuel in the cylinder can be improved. Therefore, the development of such sensors is vital to the national economy and other areas. At present, this type of sensor has been used in engines for spacecraft, aircraft, and automobiles, and been extensively used in the study of the engines, in some countries.

However, the properties of materials are different under a high temperature and under a normal temperature, in other words, the properties of materials vary with temperature. For example, some materials that are insulators under normal temperatures may become conductors under a high temperature. Therefore, in order to use high-temperature materials in a high temperature environment, the properties of such materials under high temperatures shall be detected at first, namely determining the variation with temperature of some property of such a material, especially the variation with temperature under high temperatures (400° C.~1600° C.).

Conventional testing of material properties is a regular testing generally carried out at a lower temperature (<400° C.). In order to test the properties of material at a high temperature, it is necessary to introduce a test system capable of operating at a high temperature. However, the test instruments are readymade in this test system, lacking a fixture for placing a sample at a high temperature. Although there are reports on testing the material properties at a high temperature in some countries, none provide relevant information on corresponding fixtures. In China, applications in the high-temperature field have just begun. Lack of a fixture for testing the property of a material at a high temperature directly led to the rarity of information on high-temperature property testing.

Testing of high-temperature properties of materials usually needs to go through a process of heating—testing—cooling, while the period for heating and cooling usually takes up more than 80% of the whole testing period, resulting in a low efficiency of the test. Accordingly, there is an urgent need in the art for a fixture that can improve the efficiency of the test.

SUMMARY OF THE INVENTION

The present invention aims at overcoming the shortcomings of conventional fixtures for testing the electrical properties of materials at a high temperature, and provides a fixture suitable for testing the electrical properties of materials at a high temperature.

The present invention provides a fixture suitable for testing electrical properties of materials at a high temperature, said fixture comprising: at least three noble metal electrodes arranged in parallel, among which two adjacent noble metal electrodes are used for clamping a test sample; noble metal wires connected to the noble metal electrodes at one end, and to a test device at the other end for transmitting test signals generated by the test sample to the test device through the noble metal electrodes; and a thermocouple for measuring the temperature of the test materials.

During testing, the test materials clamped between the noble metal electrodes are placed in a high-temperature furnace, which is heated up continuously according to test requirements. At the same time, a resistance test instrument is connected with the noble metal wires that are connected to the metal electrodes, and the thermocouple is connected with a temperature display device. When the temperature display device shows the test material has reached a desired temperature, the value on the resistance test instrument at this time is recorded to give the electrical property of the tested material at the temperature. The electrical properties of the tested material at different temperatures can be obtained by controlling the high-temperature furnace in such a manner that test materials reach different temperatures. Since the fixture of the present invention is provided with at least three noble metal electrodes arranged in parallel, it is possible to form at least two clamping units, and therefore, by using the fixture of the present invention, the experimenter can simultaneously test the electrical properties of two or more test materials at different temperatures.

Preferably, the noble metal electrodes comprise a first electrode, a second electrode and at least one third shared electrode; and the first electrode and the at least one third shared electrode are arranged to be movable in a direction perpendicular to the noble metal electrode so that the distance between each of the noble metal electrodes is adjustable.

In the present invention, two adjacent clamping units share a noble metal electrode, making it possible to reduce the manufacturing cost of the fixture and to make the fixture structure compact. At the same time, the distance between the noble metal electrodes can be adjusted, making it possible to test different sizes.

Preferably, said fixture further comprises a protection tube surrounding a first wire that is connected to the first electrode, the protection tube is movable in a direction perpendicular to the noble metal electrodes, and the first electrode is provided at the end surface of the protection tube.

The protection tube surrounding the wire serves to prevent the wires from contacting each other, thereby preventing a short circuit. The protection tube can be made of high-temperature resistant insulating ceramics such as high purity alumina ceramics or zirconia ceramics. The high purity alumina ceramics can be used at any temperature up to 1900° C., and can be used in any atmosphere. The high purity zirconia ceramics can be used at any temperature up to 2300° C. and can be used in any atmosphere. The first electrode is provided on the end surface of the protection tube, thus the movement of the first electrode can be realized by moving the protection tube.

Preferably, said fixture further comprises a frame-shaped bracket having an opening, and the noble metal electrodes extend toward the opening.

In the present invention, a frame-shaped bracket is provided for limiting the volume of the entire fixture, thus the manufacturing cost of the fixture can be reduced, and the structure of the fixture can be made compact. The test sample can be conveniently placed into and removed from the fixture through the opening.

Preferably, said fixture further comprises an electrode holder for supporting the second electrode and the third shared electrode, the electrode holder is fixed to the frame-shaped bracket and configured to extend in a direction perpendicular to the noble metal electrodes, the second electrode is fixed at one end of the electrode holder, and the electrode holder further comprises a sliding slot, in which an end of the third shared electrode is slidably accommodated, so that the third shared electrode is movable in a direction perpendicular to the noble metal electrodes.

By securing the electrodes in the above-described manner, a solid structure of the electrodes and the electrode holder can be easily realized, and the performance thereof can be stabilized. The second electrode is slidably disposed on the electrode holder, therefore, when the test sample between the first electrode and the second electrode is pressed by the first electrode, the second electrode may be further pressed to move along the sliding slot.

Preferably, said fixture further comprises a first wire bracket, which is fixed to the frame-shaped bracket for supporting the noble metal wires, the thermocouple, and the protection tube, and has a plurality of through-holes corresponding to the noble metal wires, the thermocouple, and the protection tube, respectively.

The first wire bracket provided in the above-described manner can support the noble metal wires, the thermocouple, and the protection tube, and can compact the fixture structure.

Preferably, said fixture further comprises a second wire bracket fixed to said electrode holder, which has a plurality of through-holes corresponding to the thermocouple, a second wire connected to the second electrode, and/or a third wire connected to the third shared electrode, respectively.

The second wire bracket provided in the above-described manner may assist in supporting the thermocouple, the second wire connected to the second electrode, and/or the third wire connected to the third shared electrode, enabling further compacting of the fixture structure.

Preferably, the fixture further comprises a spring (high-temperature resistant spring), one end of which is connected to the first wire bracket and the other end of which is connected to the protection tube.

In the fixture of the invention a spring is provided as a pressure-application unit so that the electrode and the test sample can contact each other tightly and firmly when the sample is tested, so as to ensure the reliability and efficiency of the test result.

Preferably, the material of the noble metal electrodes and/or the noble metal wires is platinum or iridium.

The platinum can be used in an oxidizing, reducing or inert atmosphere, and its melting point is 1773° C.; The iridium can only be used in a reducing or inert atmosphere, and its melting point is 2454° C. The noble metal electrodes or the noble metal wires made of the above material have a high melting point, therefore the technical object of the present invention can be achieved.

Preferably, the thermocouple is of S-type, B-type, or made of tungsten-rhenium.

The thermocouple is used to provide real-time temperature signal of the test sample. When connected to a corresponding instrument, it may display real-time temperature of the sample. The thermocouple may be of S-type, B-type, or tungsten-rhenium type, etc., which can be used at a temperature up to 1600° C. The testing range of the S-type thermocouple is 0~1600° C.; the testing range of the B-type thermocouple is 0~1800° C.; the testing range of the tungsten-rhenium thermocouple is 0~2300° C. However, the tungsten-rhenium thermocouple cannot be used in an oxidizing atmosphere.

Preferably, the protection tube, the frame-shaped bracket, the electrode holder, the first wire bracket and/or the second wire bracket is made of high-temperature resistant insulating ceramics.

Since the fixture in the present invention is used at a high temperature and the above-mentioned components need to be insulating material, the above-described components can be made of high-temperature resistant insulating ceramics.

Preferably, said high-temperature resistant insulating ceramics include alumina ceramics and zirconia ceramics.

The high purity alumina ceramics can be used at any temperature up to 1900° C. in any atmosphere. The high purity zirconia ceramics can be used at any temperature up to 2300° C. in any atmosphere.

Advantageous effects of the invention: The high-temperature test fixture according to the invention can meet the requirements for testing electrical and electrical-related properties of samples under a high temperature environment (400° C.~2300° C.). In addition, since this high-temperature fixture can simultaneously test the properties of two samples, the test efficiency can be greatly improved.

BRIEF DESCRIPTION OF THE DRAWINGS

FIG. 1 shows a structural representation of a fixture suitable for testing the electrical properties of a material at a high temperature in accordance with an embodiment of the present invention.

1—noble metal wire; 2—noble metal wire; 3, 4—two electrodes of thermocouple; 5—noble metal wire; 6—protection tube; 7—(frame-shaped) bracket; 8, 10, 14, 16—wire bracket (fixing device); 15—electrode holder (fixing device); 9—high-temperature resistant spring; 11, 12, 13—noble metal electrode.

DETAILED DESCRIPTION OF THE EMBODIMENTS

Hereinafter, the invention will be further described with reference to the accompanying drawings and the following embodiments, and it should be understood that the following embodiments are only used to explain this invention and do not limit the scope of this invention.

The invention relates to a fixture suitable for testing the electrical properties of a test material at high temperature conditions (operating temperature 400° C. to 2300° C.), so as to meet the requirements for fixtures when testing sample properties in high temperature environments. The test of high-temperature properties of materials usually needs to go through a process of heating—testing—cooling, during which the heating/cooling rate cannot be too high since a precise control of the temperature is required, thus during test, the period for heating and cooling usually takes up more than 80% of the whole testing duration, resulting in a low efficiency of the test. In view of the shortcomings of the long heating/cooling period when testing the high-temperature properties of a material, the invention can test the properties of two pieces of samples at the same time owing to the ingenious design of the high-temperature fixture, which greatly improves the testing efficiency.

FIG. 1 shows an exemplary structure of a high-temperature test fixture of the present invention. By selecting different noble metals, thermocouples, and high-temperature insulating ceramics materials, the fixture can be used in different temperatures. For example, when choosing platinum, an S-type thermocouple, and alumina ceramics, the maximum operating temperature of the fixture is around 1600° C.; when choosing iridium, a tungsten-rhenium thermocouple, and zirconia ceramics, the maximum operating temperature of the fixture can reach 2300° C. or so in an oxidizing atmosphere. Noble metals have a favorable high-temperature conductivity, and can provide an electrical signal circuit.

Referring to FIG. 1, the fixture may include a plurality of noble metal electrodes 11, 12, 13 arranged in parallel (e.g., vertically, as shown in FIG. 1), which are in contact with and sandwich the sample, transferring signals generated by the sample to a test instrument effectively and reliably. The fixture includes at least three noble metal electrodes so that at least two samples can be clamped, for example, referring to FIG. 1, the noble metal electrodes 11, 12 may constitute a clamping unit, and the noble metal electrodes 12, 13 constitute another clamping unit. The two clamping units are adjacent to each other, sharing the noble metal electrode 12. It is to be understood that the number of the noble metal electrodes is not limited to three, for example, four or five noble metal electrodes may be used for clamping three or four test samples at the same time. The noble metal electrodes 11, 12, 13 are made of platinum (Pt) or iridium (Ir) which is high-temperature resistant. The platinum can be used in an oxidizing, reducing or inert atmosphere, and its melting point is 1773° C. The iridium can only be used in a reducing or inert atmosphere, and its melting point is 2454° C. The noble metal electrodes 11, 12 can be moved in a direction perpendicular to the noble metal electrodes (for example, in the horizontal direction shown in FIG. 1) to match with different sizes of test samples. In an example, the noble metal electrode (first electrode) 11 can be moved horizontally by an external force, and the noble metal electrode (third shared electrode) 12 can be moved by the pushing of the first electrode. The noble metal electrode (second electrode) 13 is preferably fixed.

Each noble metal electrode 11, 12, 13 has a noble metal wire 5, 2, 1 connected thereto, respectively. The noble metal wire (first wire) 5 is mainly used for connecting with the noble metal electrode (first electrode) 11 and collecting the signal obtained from the electrode 11. The noble metals can be platinum (Pt) or iridium (Ir) which is high-temperature resistant. The platinum can be used in an oxidizing, reducing or inert atmosphere, and its melting point is 1773° C. The iridium can only be used in a reducing or inert atmosphere, and its melting point is 2454° C. The free end of the noble metal wire 5 may have a terminal c, which may be used to connect with an external test instrument.

The noble metal wire (second wire) 1 is mainly used for connecting with the noble metal electrode (second electrode) 13 and collecting the signal from the electrode 13. The noble metal wire 1 can be made of platinum (Pt) or iridium (Ir) which is high-temperature resistant. The platinum can be used in an oxidizing, reducing or inert atmosphere, and its melting point is 1773° C. The iridium can only be used in a reducing or inert atmosphere, and its melting point is 2454° C. The free end of the noble metal wire 1 may have a terminal a, which may be used to connect with an external test instrument.

Referring again to FIG. 1, the fixture is provided with a noble metal wire (third wire) 2, mainly for connecting with the noble metal electrode 13 and collecting the signal obtained from the electrode 13. The noble metals can be platinum (Pt) or iridium (Ir) which is high-temperature resistant. The platinum can be used in an oxidizing, reducing or inert atmosphere, and its melting point is 1773° C. The iridium cannot be used in an oxidizing atmosphere, and its melting point is 2454° C. The free end of the noble metal wire 2 may have a terminal b, which may be used to connect with an external test instrument.

Referring again to FIG. 1, the fixture has two electrodes 3, 4 of the thermocouple, which serve to provide a real-time temperature signal of the test sample, by connecting to a corresponding meter on which the real-time temperature of the sample can be displayed. The thermocouple can be S-type, B-type, tungsten-rhenium thermocouple, etc., which can be used at a temperature up to 1600° C. The testing range of the S-type thermocouple is 0~1600° C.; the testing range of the B-type thermocouple is 0~1800° C.; and the testing range of the tungsten-rhenium thermocouple is 0~2300° C. However, the tungsten-rhenium thermocouple cannot be used in an oxidizing atmosphere.

The noble metal wire (first wire) 5 may have a protection tube 6 which surrounds the noble metal wire (first wire) 5 and serves to prevent the terminal c and its connecting wire from coming into contact with other connecting wires and resulting in a short circuit and a test failure. In addition, the protection tube 6 is used for fixing the high-temperature resistant spring 9. The protection tube 6 may be made of high-temperature resistant insulating ceramics such as high purity alumina ceramics or zirconia ceramics. The high purity alumina ceramics can be used at a temperature up to 1900° C., in any atmosphere. The high purity zirconia ceramics can be used at a temperature up to 2300° C., in any atmosphere. The protection tube 6 may also be arranged to be movable in a direction perpendicular to the electrodes (for example, in the horizontal direction), and the first electrode 11 may be provided at the end surface of the protection tube 6 so as to be movable by pulling or pushing the protection tube 6.

The high-temperature fixture may further include a (frame-shaped) bracket 7 which serves to provide support for other components of the fixture, and may be made of high-temperature resistant insulating ceramics such as high purity alumina ceramics or zirconia ceramics. The high purity alumina ceramics can be used at a temperature up to 1900° C., in any atmosphere. The high purity zirconia ceramics can be used at a temperature up to 2300° C., in any atmosphere. The (frame-shaped) bracket 7 may have an opening toward which the noble metal electrodes 11, 12, 13 extend so as to facilitate introduction of the test sample.

The high-temperature fixture may further include fixing devices 8, 10, 14, 15, 16 providing support for corresponding components, and made of high-temperature resistant insulating ceramics such as high purity alumina ceramics or zirconia ceramics, etc.; the high purity alumina ceramics can be used at a temperature up to 1900° C., in any atmosphere. The high purity zirconia ceramics can be used at a temperature up to 2300° C., in any atmosphere.

A fixing device (first wire bracket) 8 is fixed to the high-temperature bracket 7 for supporting the noble metal wires 1 and 2, the thermocouple, the noble metal wire 5, the protection tube 6, and the high-temperature resistant spring 9; for example, the fixing device (first wire bracket) 8 may have a plurality of through-holes through which the metal wires 1 and 2, the thermocouples, the noble metal wire 5 and the protection tube 6 pass, respectively.

One or more fixing devices (first wire bracket) 10 for assisting in supporting the noble metal wires 1 and 2, the thermocouple, the noble metal wire 5, and the protection tube 6, may be fixed to the high-temperature bracket 7; for example, a plurality of through-holes may be formed in the fixing device (first wire bracket) 10, and the metal wires 1 and 2, the thermocouple, the noble metal wire 5, and the protection tube 6 may pass through said plurality of through-holes, respectively.

A fixing device (electrode holder) 15 is fixed to the high-temperature bracket 7, and the fixing device (electrode holder) 15 is configured to extend in a direction perpendicular to the direction of the electrodes (e.g., the horizontal direction shown in FIG. 1), for supporting the second electrode 13 and the third shared electrode 12 in which the second electrode 13 can be fixed to the electrode holder 15 and the third shared electrode 12 can be slidably supported on the electrode holder 15, for example, the electrode holder 15 may have a sliding slot, and the end of the third shared electrode 12 (e.g., the lower end portion) can slide in the sliding slot.

The fixture may further include a fixing device 14. A second wire bracket (fixing device) 14, 16 fixed on the fixing device (electrode holder) 15 is used for supporting the thermocouple, a second wire 1 connected to the second electrode 13, and/or a third wire 2 connected to the third shared electrode 12; for example, the fixing device 14 is used for supporting thermocouples, and the fixing device (second wire bracket) 14 may have a plurality of through-holes through which the thermocouples pass, respectively; for example, the fixing device 16 is used for supporting the second wire 1 connected to the second electrode 13, and the third wire 2 connected to the third shared electrode 12, and the fixing device (second wire bracket) 16 may also have a plurality of through-holes through which the wires 1, 2 pass, respectively.

The high-temperature resistant spring 9 can be secured to the protection tube 6 and the fixing device 8, that is, one end of the spring 9 is connected to the first wire bracket 8 and the other end is connected to the protection tube 6, so that a pressure can be applied to the noble metal electrode 11, thus the noble metal electrodes 11, 12, 13 can tightly and firmly contact the test sample during testing to ensure the reliability and effectiveness of the test results. By pulling or pushing the protection tube 6, the force applied to the first electrode 11 from the protection tube 6 can be adjusted.

The test samples are placed between the noble metal electrodes 11, 12, and between the noble metal electrodes 12, 13 during the test. And then a test circuit is connected in accordance with the requirements for testing properties to test the corresponding properties of the sample. The sample placed between the noble metal electrodes 11, 12 is tested when the two poles of the test circuit is connected to the terminal c and the terminal b; the sample placed between the noble metal electrodes 12, 13 is tested when the two poles of the test circuit is connected to the terminal b and the terminal a; if the two poles of the test circuit is connected to the terminal c and the terminal a, the test result is equivalent to the result in the case that the two samples are connected in series. When there is only one test sample, it can be discretionarily placed between the noble metal electrodes 11, 12, or between the noble metal electrodes 12, 13. If a sample is placed between the noble metal electrodes 11, 12, the two poles of the test circuit must be connected to terminal c and terminal b; however, if the sample is placed between the noble metal electrodes 12, 13, the two poles of the test circuit must be connected to the terminal b and the terminal a.

Hereinafter, the present invention will be better illustrated with the following exemplary examples. It is to be understood that the foregoing descriptions of the embodiments of the present invention, as well as the following examples, are intended to illustrate the present invention and do not limit the scope of the invention. Any non-essential improvements and modifications made by a person skilled in the art based on this invention all fall into the protection scope of this invention. The specific parameters below such as proportion, temperature, time and the like are only exemplary, and a person skilled in the art can choose proper values within the above-defined ranges.

If choosing platinum as the noble metal for the high-temperature fixture, S-type thermocouple as the thermocouple, and high-purity alumina ceramics as the high-temperature resistant insulating ceramics, the operating temperature of the fixture can be up to 1600° C. or so, and any atmosphere can be used. Specific test procedures are described in Examples 1, 2, and 3.

If choosing iridium as the noble metal for the high-temperature fixture, tungsten-rhenium thermocouple as the thermocouple, and zirconia ceramics as the high-temperature resistant insulating ceramics, the operating temperature of the fixture can be up to 2300° C. or so, but it cannot be used in an oxidizing atmosphere. Specific test procedures are described in Examples 1, 2, and 3.

EXAMPLE 1

Testing the Resistance of Two Wafers at a Specific Temperature at the Same Time

Step 1: The high-temperature fixture was taken out, and the protection tube 6 was pulled to the left, then two samples to be tested were placed between the noble metal electrodes 11, 12, and between the noble metal electrodes 12, 13, respectively. The entire high-temperature fixture was put into a high-temperature furnace, while the terminals a, b of the noble metal wires 1, 2, the two poles 3, 4 of the thermocouple, and the terminal c of the noble metal wire 5 were exposed to the outside of the furnace cavity through the furnace body.

Step 2: The two poles 3, 4 of the thermocouple were connected with a temperature display device, which displays the real-time temperature of the sample being tested.

Step 3: The furnace was turned on and heated up. When the temperature of the test samples reached the desired temperature, the terminals a, b of the noble metal wires 1, 2 were connected to a resistance testing instrument so that the resistance value of the sample between the noble metal electrodes 12, 13 can be read; and then the terminal a of the noble metal wire 1 was disconnected, and the terminals b, c of the noble metal wires 2, 5 were connected to the resistance testing instrument, so that the resistance value of the sample between the noble metal electrodes 11, 12 can be read.

Step 4: The furnace was turned off and cooled down. When the temperature of the samples dropped to or close to the room temperature, the high-temperature fixture and the samples were taken out, and the test work was completed.

EXAMPLE 2

Testing the Variation of the Resistivity of Two Wafers with Temperature at the Same Time Step 1: The high-temperature fixture was taken out, and the protection tube 6 was pulled to the left, then two samples to be tested were placed between the noble metal electrodes 11, 12, and between the noble metal electrodes 12, 13, respectively. The entire high-temperature fixture was put into a high-temperature furnace, while the terminals a, b of the noble metal wires 1, 2, the two poles 3, 4 of the thermocouple, and the terminal c of the noble metal wire 5 were exposed to the outside of the furnace cavity through the furnace body.

Step 2: The two poles 3, 4 of the thermocouple were connected with a temperature display device, which displays the real-time temperature of the sample being tested.

Step 3: The furnace was turned on and heated up, and the temperature of the high-temperature furnace was set, so that the temperature of the test samples reached a first desired temperature.

Step 4: The terminals a, b of the noble metal wires 1, 2 were connected to a resistance testing instrument, so that the resistance value of the sample between the noble metal electrodes 12, 13 can be read, and then the terminal a of the noble metal wire 1 was disconnected, and the terminals b, c of the noble metal wires 2, 5 were connected to the resistance testing instrument, so that the resistance value of the sample between the noble metal electrodes 11, 12 can be read. The resistivity of the samples at this temperature was calculated according to the resistance value tested, and the sample dimensions.

Step 5: The temperature of the high-temperature furnace was set so that the temperature of the samples reached a second desired temperature. Step 4 was repeated until all tests at each desired temperature had been completed.

Step 6: The furnace was turned off and cooled down. When the temperature of the samples dropped to or close to the room temperature, the high-temperature fixture and the samples were taken out, and the test work was completed.

EXAMPLE 3

Testing the Resistivity of a Piece of Ceramic Chip at a Specific Temperature

Step 1: The high-temperature fixture was taken out, and the protection tube 6 was pulled to the left, then the sample to be tested was placed between the noble metal electrodes 11, 12, or between the noble metal electrodes 12, 13, respectively. The entire high-temperature fixture was put into a high-temperature furnace, while the terminals a, b of the noble metal wires 1, 2, the two poles 3, 4 of the thermocouple, and the terminal c of the noble metal wire 5 were exposed to the outside of the furnace cavity through the furnace body.

Step 2: The two poles 3, 4 of the thermocouple were connected with a temperature display device, which displays the real-time temperature of the sample being tested.

Step 3: The furnace was turned on and heated up. When the temperature of the test sample reached the desired temperature, the terminals b, c of the noble metal wires 2, 5 were connected to a resistance testing instrument if the sample was placed between the noble metal electrodes 11, 12, the resistance value of the sample was read and the resistivity of the sample was calculated according to the resistance value and the dimensions of the sample; or, the terminals a, b of the noble metal wires 1, 2 were connected to the resistance testing instrument if the sample was placed between the noble metal electrodes 12, 13, the resistance of the sample was read and the resistivity of the sample was calculated according to the resistance value and the dimensions of the sample.

Step 4: The furnace was turned off and cooled down. When the temperature of the samples dropped to or close to the room temperature, the high-temperature fixture and the samples were taken out, and the test work was completed.

What is claimed is:

1. A fixture suitable for testing electrical properties of a test sample at a high temperature, said fixture comprising:
    at least three noble metal electrodes arranged in parallel, among which two adjacent noble metal electrodes are used for clamping the test sample;
    noble metal wires connected to the noble metal electrodes at one end, and to a test device at the other end for transmitting test signals generated by the test sample to the test device through the noble metal electrodes; and
    a thermocouple for measuring the temperature of the test sample.

2. The fixture of claim 1, wherein the noble metal electrodes comprise a first electrode, a second electrode and at least one third shared electrode; and
    wherein the first electrode and the at least one third shared electrode are arranged to be movable in a direction perpendicular to the noble metal electrodes so that the distance between each of the noble metal electrodes is adjustable.

3. The fixture of claim 2, wherein said fixture further comprises a protection tube surrounding a first wire that is connected to the first electrode, the protection tube is movable in a direction perpendicular to the noble metal electrodes, and the first electrode is provided at the end surface of the protection tube.

4. The fixture of claim 3, wherein said fixture further comprises a frame-shaped bracket having an opening, and wherein the noble metal electrodes extend toward the opening.

5. The fixture of claim 4, wherein said fixture further comprises an electrode holder for supporting the second electrode and the third shared electrode, the electrode holder is fixed to the frame-shaped bracket, and configured to extend in a direction perpendicular to the noble metal electrodes, and the second electrode is fixed at one end of the electrode holder, and wherein the electrode holder further comprises a sliding slot, in which an end of the third shared electrode is slidably accommodated so that the third shared electrode is movable in a direction perpendicular to the noble metal electrodes.

6. The fixture of claim 5, wherein said fixture further comprises a first wire bracket fixed to the frame-shaped bracket for supporting the noble metal wires, the thermocouple, and the protection tube, and wherein the first wire bracket has a plurality of through-holes corresponding to the noble metal wires, the thermocouple, and the protection tube, respectively.

7. The fixture of claim 6, wherein said fixture further comprises a second wire bracket fixed to said electrode holder, and wherein said second wire bracket has a plurality of through-holes corresponding to the thermocouple, and at least one of a second wire connected to the second electrode, and a third wire connected to the third shared electrode.

8. The fixture of claim 6, wherein the fixture further comprises a spring, one end of which is connected to the first wire bracket and the other end of which is connected to the protection tube.

9. The fixture of claim 1, wherein the material of at least one of the noble metal electrodes and the noble metal wires is platinum or iridium.

10. The fixture of claim 1, wherein the thermocouple is of S-type, B-type, or made of tungsten-rhenium.

11. The fixture of claim 7, wherein at least one of the protection tube, the frame-shaped bracket, the electrode holder, the first wire bracket, and the second wire bracket is made of high-temperature resistant insulating ceramics.

12. The fixture of claim 11, wherein said high-temperature resistant insulating ceramics include alumina ceramics and zirconia ceramics.

* * * * *